(12) United States Patent
Rudolf et al.

(10) Patent No.: US 8,716,277 B2
(45) Date of Patent: May 6, 2014

(54) SUBSTITUTED IMIDAZOLE COMPOUNDS USEFUL AS POSITIVE ALLOSTERIC MODULATORS OF MGLU5 RECEPTOR ACTIVITY

(71) Applicants: Klaus Rudolf, Warthausen (DE); Daniel Bischoff, Biberach an der Riss (DE); Georg Dahmann, Warthausen-Birkenhard (DE); Matthias Grauert, Biberach an der Riss (DE); Raimund Kuelzer, Mittelbiberach (DE); Bernd Wellenzohn, Friedrichshafen (DE)

(72) Inventors: Klaus Rudolf, Warthausen (DE); Daniel Bischoff, Biberach an der Riss (DE); Georg Dahmann, Warthausen-Birkenhard (DE); Matthias Grauert, Biberach an der Riss (DE); Raimund Kuelzer, Mittelbiberach (DE); Bernd Wellenzohn, Friedrichshafen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/709,330

(22) Filed: Dec. 10, 2012

(65) Prior Publication Data

US 2013/0158011 A1  Jun. 20, 2013

(30) Foreign Application Priority Data

Dec. 14, 2011 (EP) ...................................... 11193380

(51) Int. Cl.
| | |
|---|---|
| C07D 513/04 | (2006.01) |
| C07D 498/04 | (2006.01) |
| C07D 413/14 | (2006.01) |
| C07D 403/06 | (2006.01) |
| C07D 413/12 | (2006.01) |
| C07D 233/64 | (2006.01) |
| A61K 31/424 | (2006.01) |
| A61K 31/429 | (2006.01) |
| A61K 31/437 | (2006.01) |
| A61K 31/496 | (2006.01) |
| A61K 31/55 | (2006.01) |

(52) U.S. Cl.
USPC .................. 514/215; 514/254.04; 514/254.05; 514/302; 514/367; 544/368; 544/370; 546/115; 548/153

(58) Field of Classification Search
USPC .................. 548/153; 544/370, 368; 546/115; 514/215, 254.4, 254.5, 367, 302; 504/578; 540/578
See application file for complete search history.

(56) References Cited

U.S. PATENT DOCUMENTS

| | | | |
|---|---|---|---|
| 6,166,008 A | 12/2000 | Johnson et al. | |
| 7,582,635 B2 | 9/2009 | Sun et al. | |
| 8,008,300 B2 | 8/2011 | Sun et al. | |
| 8,048,890 B2 | 11/2011 | Buschmann et al. | |
| 2003/0055085 A1 | 3/2003 | Wagenen et al. | |
| 2004/0186111 A1 | 9/2004 | Sun et al. | |
| 2005/0256130 A1 | 11/2005 | Pennell et al. | |
| 2007/0154428 A1 | 7/2007 | Sato et al. | |
| 2010/0004254 A1 | 1/2010 | Sun et al. | |
| 2010/0216787 A1 | 8/2010 | Sato et al. | |
| 2012/0004217 A1 | 1/2012 | Sun et al. | |
| 2012/0015954 A1 | 1/2012 | Sun et al. | |
| 2013/0137688 A1 | 5/2013 | Grauert et al. | |
| 2013/0143870 A1 | 6/2013 | Grauert et al. | |
| 2013/0150341 A1 | 6/2013 | Grauert et al. | |
| 2013/0150347 A1 | 6/2013 | Rudolf et al. | |
| 2013/0150355 A1 | 6/2013 | Rudolf et al. | |
| 2013/0158011 A1 | 6/2013 | Rudolf et al. | |
| 2013/0158038 A1 | 6/2013 | Rudolf et al. | |
| 2013/0184248 A1 | 7/2013 | Grauert et al. | |

FOREIGN PATENT DOCUMENTS

| | | |
|---|---|---|
| CA | 2476031 A1 | 9/2003 |
| EP | 0307145 A1 * | 9/1988 |
| EP | 0919232 A1 * | 6/1999 |
| WO | 9749395 | 12/1997 |

(Continued)

OTHER PUBLICATIONS

Adams et al. "Chlorpromazine versus placebo for schizophrenia (Review)." The Cochrane Library, pp. 1-3 (summary), Jul. 8, 2009 [online]. Nottingham, U.K.: John Wiley & Sons, Ltd. [retrieved on Aug. 7, 2013]. Retrieved from http://onlinelibrary.wiley.com/doi/10.1002/14651858.CD000284.pub2/abstract;jsessionid=F864DDF30197DD44ED13C240C643AB1A.d01t02.*

(Continued)

*Primary Examiner* — Samantha Shterengarts
*Assistant Examiner* — Amanda L Aguirre
(74) *Attorney, Agent, or Firm* — Michael P. Morris; Anthony P. Bottino

(57) ABSTRACT

This invention relates to compounds of formula I

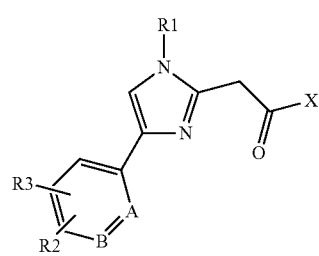

their use as positive allosteric modulators of mGlu5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment. A, B, X, $R^1$, $R^2$, $R^3$ have meanings given in the description.

4 Claims, No Drawings

(56) References Cited

FOREIGN PATENT DOCUMENTS

| WO | 0206288 A1 | 1/2002 |
|---|---|---|
| WO | 03051833 A2 | 6/2003 |
| WO | 03053922 A2 | 7/2003 |
| WO | WO 2003076432 A1 * | 9/2003 |
| WO | 03105853 A1 | 12/2003 |
| WO | 2004058754 A1 | 7/2004 |
| WO | 2005030128 A2 | 4/2005 |
| WO | 2005056015 A1 | 6/2005 |
| WO | WO 2005085241 A1 * | 9/2005 |
| WO | 2007021573 A1 | 2/2007 |
| WO | 2007087135 A2 | 8/2007 |
| WO | 2008112440 A1 | 9/2008 |
| WO | 2008145616 A1 | 12/2008 |
| WO | 2008148840 A1 | 12/2008 |
| WO | 2008156580 A1 | 12/2008 |
| WO | 2009143404 A1 | 11/2009 |
| WO | 2010124055 A1 | 10/2010 |
| WO | 2010126811 A1 | 11/2010 |
| WO | 2011002067 A1 | 1/2011 |
| WO | 2011082010 A1 | 7/2011 |

OTHER PUBLICATIONS

Abstract in English for WO2011002067, Publication Date: Jan. 1, 2011.
Chemcats: Accession No. 0046382561, Oct. 14, 2011.
Dorwald, F. Z. "Side Reactions in Organic Synthesis: A Guide to Successful Synthesis Design." Wiley-VCH Verlag GmbH & Co. KGaA, 2005, pp. 1-390.
European Search Report for EP 11193380.0 mailed Mar. 14, 2012.
International Search Report and Written Opinion for PCT/EP2012/075312 mailed Feb. 7, 2013.
International Search Report and Written Opinion for PCT/EP2012/075313 mailed Feb. 7, 2013.
Lindsley, C.W., et al., "Discovery of Positive Allosteric Modulators for the Metabotropic Glutamate Receptor Subtype-5 from a Series of N-(1,3-Diphenyl-1H-pyrazol-5-yl) benzamides that Potentiate Receptor Function in Vivo", J. Med. Chem, 2004, 47, pp. 5825-5828.
Shasheva. E. Y. et al., "Reactions of Hydroxyphenyl-substituted 1,2,4-Triazoles with Electrophylic Reagents", Russian Journal of General Chemistry, 2009, vol. 79, No. 10, pp. 2234-2243.
Wermuth, Camille G. "Practice of Medicinal Chemistry, Third Edition." Elsevier Ltd., 2008, Ch. 6, 15, 18, and 20.

* cited by examiner

SUBSTITUTED IMIDAZOLE COMPOUNDS USEFUL AS POSITIVE ALLOSTERIC MODULATORS OF MGLU5 RECEPTOR ACTIVITY

FIELD OF THE INVENTION

This invention relates to substituted imidazoles and their use as positive allosteric modulators of mGlu5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment.

BACKGROUND OF THE INVENTION

Glutamate is the primary excitatory amino acid in the mammalian central nervous system.

Neurotransmission mediated by glutamate has been demonstrated to be critical in many physiological processes, such as synaptic plasticity, long term potentiation involved in both learning and memory as well as sensory perception (Riedel et al., Behay. Brain Res. 2003, 140:1-47). Furthermore, it has been demonstrated that an imbalance of glutamate neurotransmission plays a critical role in the pathophysiology of various neurological and psychiatric diseases.

The excitatory neurotransmission of glutamate is mediated through at least two different classes of receptors, the ionotropic glutamate receptors (NMDA, AMPA and kainate) and the metabotropic glutamate receptors (mGluR). The ionotropic receptors are ligand gated ion channels and are thought to be responsible for the regulating rapid neuronal transmission between two neurons. The metabotropic glutamate receptors are G-protein coupled receptors (GPCRs) which appear to mediate not only synaptic transmission, but also to regulate the extent of neurotransmitter release as well as post synaptic receptor activation.

Dysregulation in glutamatergic neurotransmission, for example through altered glutamate release or post-synaptic receptor activation, has been demonstrated in a variety of neurological as well as psychiatric disorders. Hypofunction of the NMDA receptor has not only been demonstrated in Alzheimer's patients, but is increasingly accepted as the putative cause of schizophrenia (Farber et al., Prog. Brain Res., 1998, 116: 421-437, Coyle et al., Cell. and Mol. Neurobiol. 2006, 26: 365-384). This is supported by clinical studies showing that antagonists of the NMDA receptor induce symptoms indistinguishable to those suffered by schizophrenia patients (Javitt et al., Am J. Psychiatry, 1991, 148: 1301-1308). Therefore, approaches that could potentiate or normalize NMDA receptor signaling have the potential to treat neurological and psychiatric disorders.

mGluR5 belongs to a superfamily of currently eight identified Type III GPCRs, which are unique in that the glutamate ligand binds to a large extracellular amino-terminal protein domain. This superfamily is further divided into three groups (Group I, II and III) based on amino acid homology as well as the intracellular signalling cascades they regulate (Schoepp et al., Neuropharma, 1999, 38:1431-1476). mGluR5 belongs to group I and is coupled to the phospholipase C signalling cascade which regulates intracellular calcium mobilization.

In the CNS, mGluR5 has been demonstrated to be expressed mainly in the cortex, hippocampus, nucleus accumbens and the caudate-putamen. These brain regions are known to be involved in memory formation and cogntive function as well as emotional response. mGluR5 has been shown to be localized post-synaptically, adjacent to the post-synaptic density (Luj an et al., Eur. J. Neurosci. 1996, 8: 1488-1500). A functional interaction between mGluR5 and the NMDA receptor has also been demonstrated, where activation of mGluR5 potentiates the activation state of the NMDA receptor (Mannaioni et al, NeuroSci., 2001, 21:5925-5924, Rosenbrock et al., Eur. J. Pharma., 2010, 639:40-46). Furthermore, activation of mGluR5 has been demonstrated in pre-clinical in vivo models to rescue cognitive impairment as well as psychotic disturbance induced by NMDA receptor antagonists (Chan et al., Psychopharma. 2008, 198:141-148). Therefore, activation of mGluR5, and thereby potentiation or normalization of the NMDA receptor signaling, is a potential mechanism for the treatment of psychiatric and neurological disorders.

Most agonists of mGluR5 bind the orthosteric glutamate binding site. Since the glutamate binding site between the mGluR family members is highly conserved, it has been challenging to develop selective mGluR5 agonists which have acceptable CNS penetration and demonstrate in vivo activity. An alternative approach to achieve selectivity between the mGluR family members is to develop compounds which bind to an allosteric site, which is not as highly conserved between the family members. These allosteric binding compounds would not interfere with the natural glutamate binding and signaling, but modulate the receptor activation state.

Positive allosteric modulators of mGluR5 have recently been identified (O'Brien et al., Mol. Pharma. 2003, 64: 731-740, Lindsley et al., J. Med. Chem. 2004, 47: 5825-5828). These compounds potentiate mGluR5 activity in the presence of bound glutamate. In the absence of bound glutamate, the mGluR5 positive modulators do not demonstrate intrinsic activity. Therefore, these compounds potentiate the natural signaling of mGluR5 as opposed to agonists which activate the receptor in a permanent, unnatural manner. mGluR5 positive allosteric modulators therefore represent an approach to potentiate mGluR5 signaling which in turn potentiates and normalizes the NMDA receptor hypofunction detected in neurological and psychiatric disorders.

DETAILED DESCRIPTION OF THE INVENTION

The present invention is directed to compounds of formula I

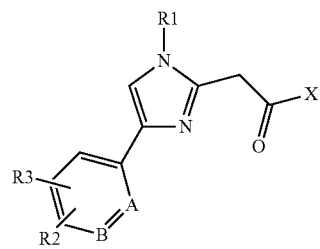

in which
A and B independently represent CH or N;
$R^1$ represents aryl, heteroaryl, $C_{1-8}$alkyl, $C_{3-7}$cycloalkyl, —O—$C_{1-8}$alkyl which latter five groups are optionally substituted with one or more substituents selected from halogen, —CN, $C_{1-3}$alkyl, —O—$C_{1-3}$alkyl;
$R^2$ and $R^3$ independently represent —H, halogen, —CN, $C_{1-5}$alkyl, $C_{3-5}$cycloalkyl, —O—$C_{1-5}$alkyl which latter three groups are optionally substituted with one or more fluorine atoms;

X represents
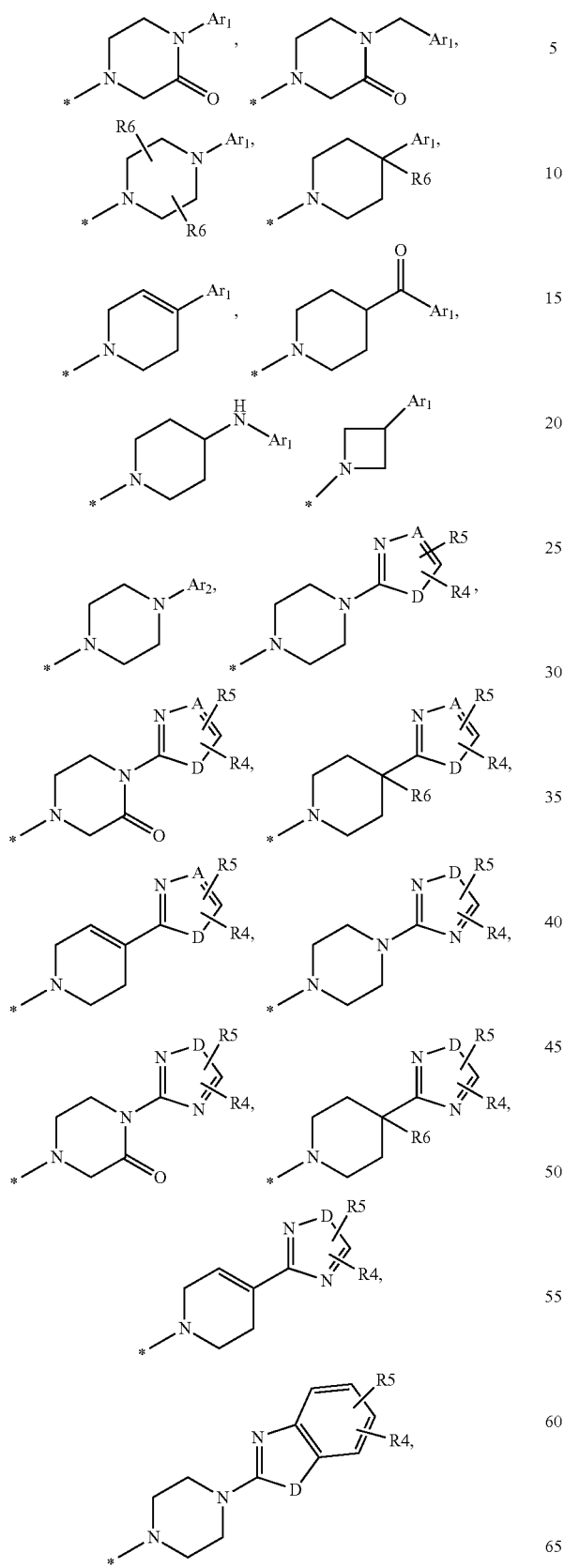
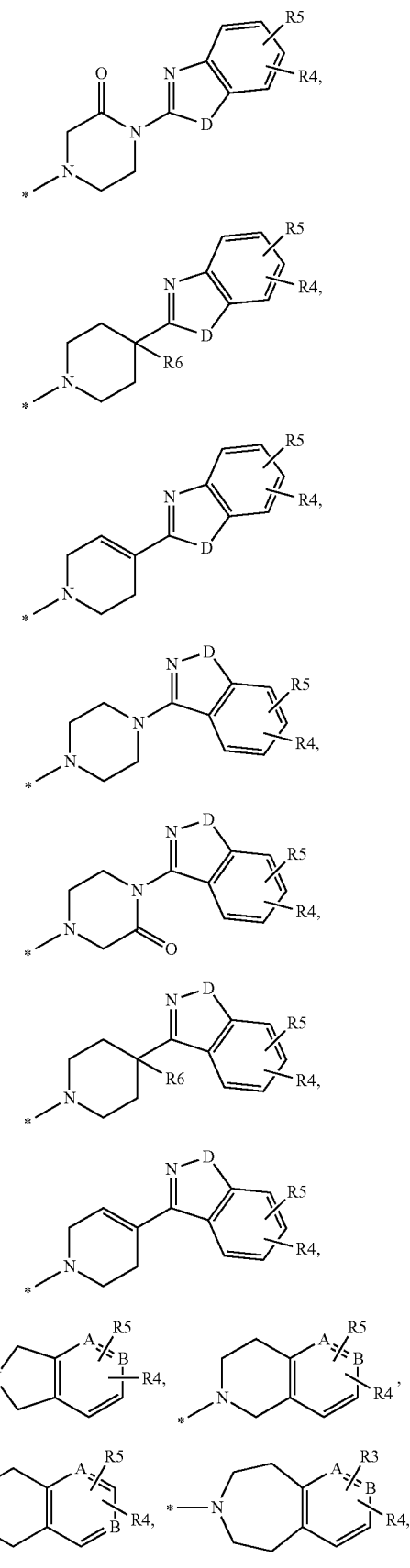

-continued

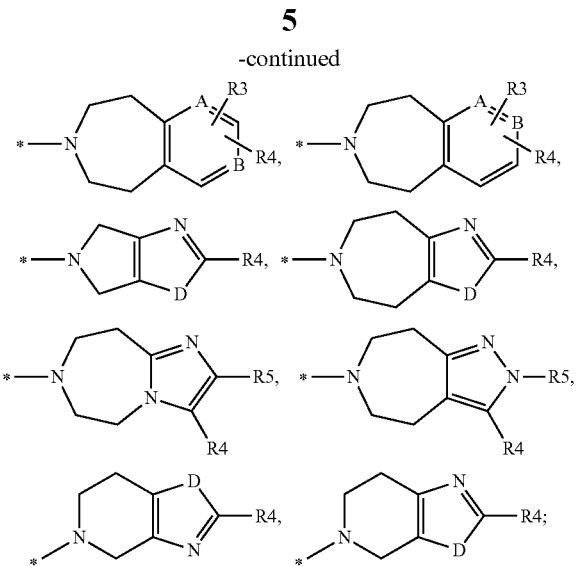

Ar₁ represents

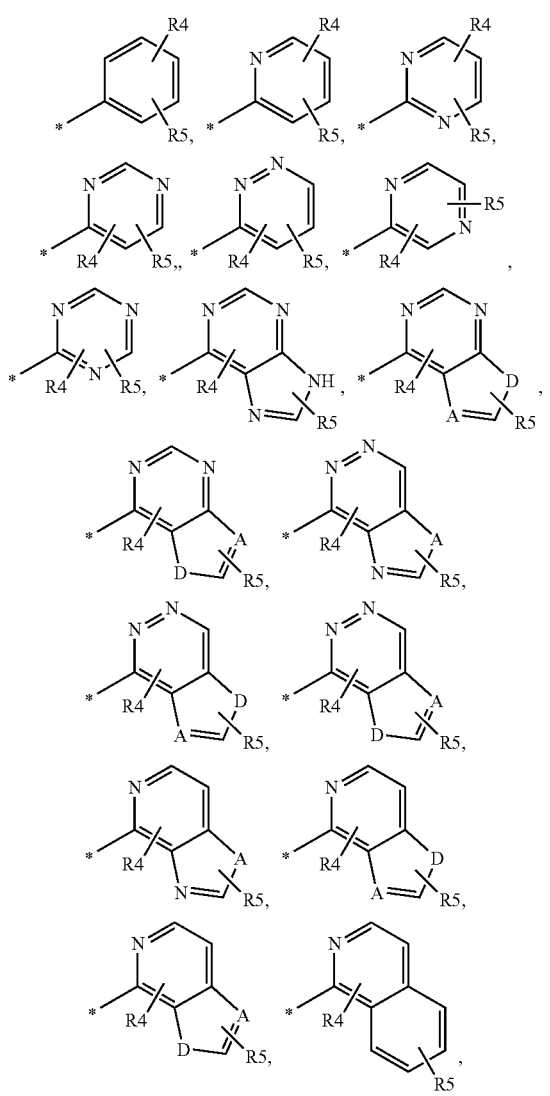

-continued

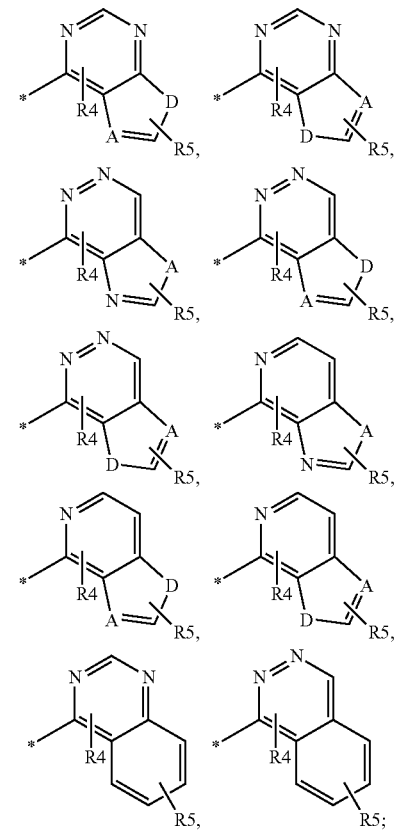

Ar₂ represents

D represents S or O,
R⁴ and R⁵ independently represent —H, halogen, —OH, —CN, —NH₂, $C_{1-5}$alkyl, phenyl, —NH—$C_{1-5}$alkyl, —N($C_{1-5}$ alkyl)₂, —O—$C_{1-5}$ alkyl, —COO—$C_{1-5}$ alkyl, —CONH($C_{1-5}$alkyl), —CON($C_{1-5}$alkyl)₂, —NH-CONH—$C_{1-5}$alkyl, —NHCON($C_{1-5}$alkyl)₂, —NHCO—$C_{1-5}$alkyl which latter eleven groups are optionally substituted with one or more substituents selected from halogen, —OH;
R⁶ represents —H, $C_{1-3}$alkyl;
or a salt thereof, particularly a physiologically acceptable salt thereof.

In another embodiment, in the general formula I, A, B, D, X, Ar¹, Ar², R², R³, R⁴, R⁵, R⁶ have the same meaning as defined in any of the preceding embodiments, and $R^1$ represents phenyl optionally substituted with one or more substituents selected from fluoro, chloro, bromo, $C_{1-3}$alkyl, —O—$C_{1-3}$ alkyl.

In another embodiment, in the general formula I, A, B, D, $Ar^1$, $R^1$, $R^2$, $R^3$, $R^4$, $R^5$, $R^6$ have the same meaning as defined in any of the preceding embodiments, and
X represents

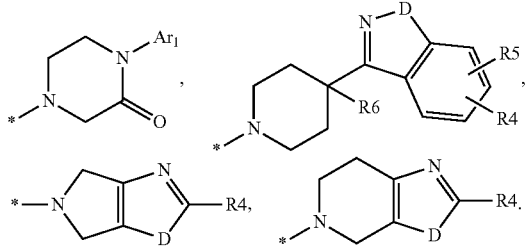

In another embodiment, in the general formula I, A, B, D, $Ar^1$, $R^1$, $R^2$, $R^3$, $R^4$, $R^5$, $R^6$ have the same meaning as defined in any of the preceding embodiments, and
X represents

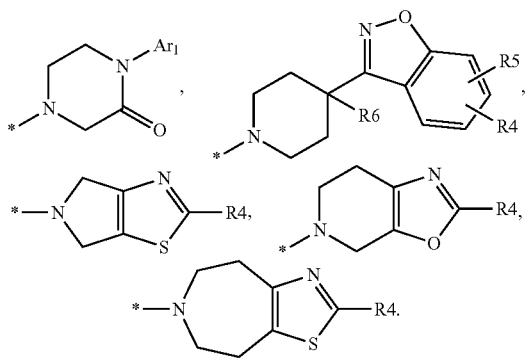

In another embodiment, in the general formula I, A, B, D, X, $Ar^2$, $R^1$, $R^2$, $R^3$, $R^4$, $R^5$, $R^6$ have the same meaning as defined in any of the preceding embodiments, and
$Ar_1$ represents

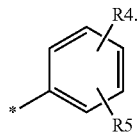

In another embodiment, in the general formula I, A, B, D, X, $Ar^1$, $Ar^2$, $R^1$, $R^2$, $R^3$, $R^4$, $R^5$ have the same meaning as defined in any of the preceding embodiments, and
$R^6$ represents hydrogen, methyl.

In another embodiment, in the general formula I, A, B, D, X, $Ar^1$, $Ar^2$, $R^1$, $R^2$, $R^3$, $R^6$ have the same meaning as defined in any of the preceding embodiments, and
$R^4$ and $R^5$ independently represent —H, —F, —Cl, —Br, —OH, —CN, —NH$_2$, $C_{1-3}$alkyl, phenyl, —NH-phenyl, —NH—$C_{1-3}$alkyl, —N($C_{1-3}$alkyl)$_2$, —O—$C_{1-3}$alkyl, —COO—$C_{1-3}$alkyl, —CONH($C_{1-3}$alkyl), —CON($C_{1-3}$alkyl)$_2$, —NHCONH—$C_{1-3}$alkyl, —NHCON($C_{1-3}$alkyl)$_2$, —NHCO—$C_{1-3}$alkyl which latter twelve groups are optionally substituted with one or more fluorine atoms.

In another embodiment, in the general formula I, A, B, D, X, $Ar^1$, $Ar^2$, $R^1$, $R^2$, $R^3$, $R^6$ have the same meaning as defined in any of the preceding embodiments, and
$R^4$ and $R^5$ independently represent —H, —CN, —NH$_2$, $C_{1-3}$alkyl, —O—$C_{1-3}$alkyl which latter two groups are optionally substituted with one or more fluorine atoms;

In another embodiment, in the general formula I, D, X, $Ar^1$, $Ar^2$, $R^1$, $R^2$, $R^3$, $R^6$ have the same meaning as defined in any of the preceding embodiments, and
A represents N or CH;
B represents CH.

In another embodiment, in the general formula I, X, $R^1$ have the same meaning as defined in any of the preceding embodiments, and the group

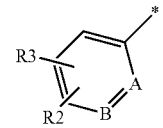

represents phenyl optionally substituted with one or more substituents selected from fluoro, chloro, bromo, —CN, $C_{1-3}$alkyl, $C_{3-5}$cycloalkyl, —O—$C_{1-3}$alkyl which latter three groups are optionally substituted with one or more fluorine atoms.

A further embodiment of the present invention comprises compounds of formula I in which
$R^1$ represents phenyl optionally substituted with one or more substituents selected from fluoro, chloro, bromo, $C_{1-3}$alkyl, —O—$C_{1-3}$alkyl;
X represents

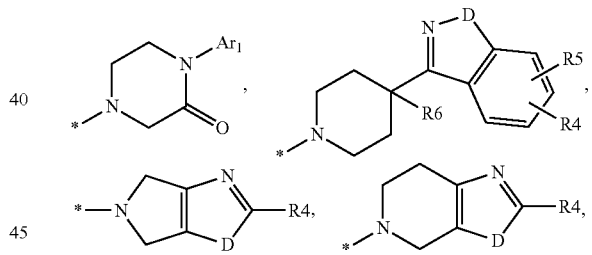

D represents O, S;
$R^4$ and $R^5$ independently represent —H, —CN, —NH$_2$, $C_{1-3}$alkyl, —O—$C_{1-3}$alkyl which latter two groups are optionally substituted with one or more fluorine atoms;
the group

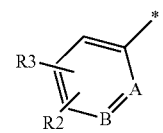

represents phenyl optionally substituted with one or more substituents selected from fluoro, chloro, bromo, —CN, $C_{1-3}$alkyl, $C_{3-5}$cycloalkyl, —O—$C_{1-3}$alkyl which latter three groups are optionally substituted with one or more fluorine atoms;
or a salt thereof, particularly a physiologically acceptable salt thereof.

In another embodiment, in the general formula I, A, B, D, X, Ar$^1$, Ar$^2$, R$^2$, R$^3$, R$^4$, R$^5$, R$^6$ have the same meaning as defined in any of the preceding embodiments, and R$^1$ represents phenyl,

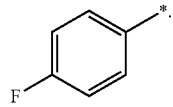

In another embodiment, in the general formula I, A, B, D, Ar$^1$, Ar$^2$, R$^1$, R$^2$, R$^3$, R$^4$, R$^5$, R$^6$ have the same meaning as defined in any of the preceding embodiments, and X represents

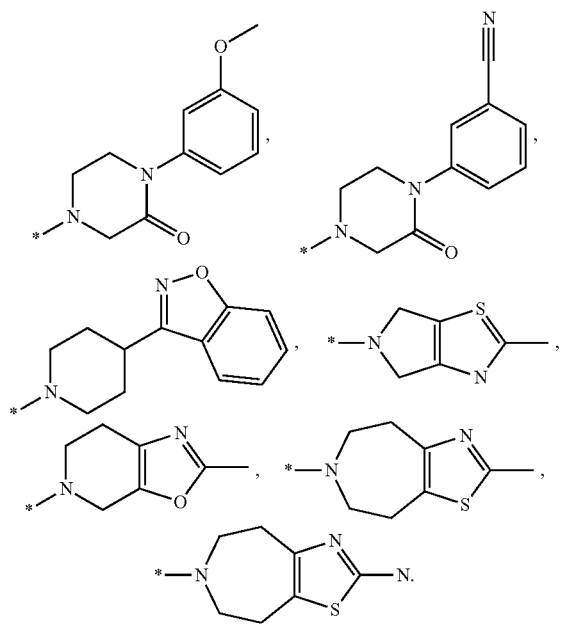

In another embodiment, in the general formula I, Ar, R$^1$ have the same meaning as defined in any of the preceding embodiments, and the group

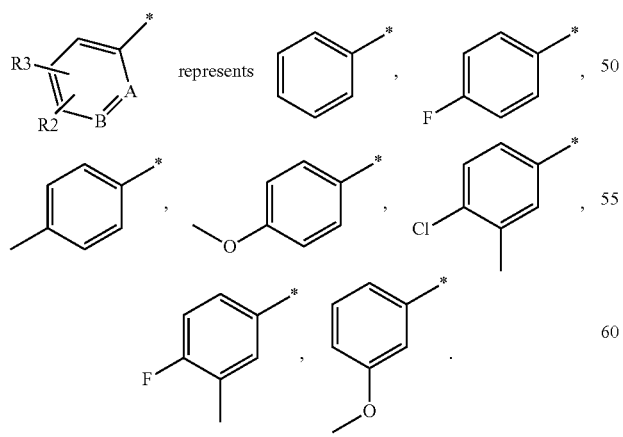

A further embodiment of the present invention comprises compounds of formula I in which R$^1$ represents phenyl,

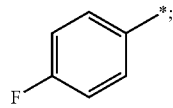

X represents

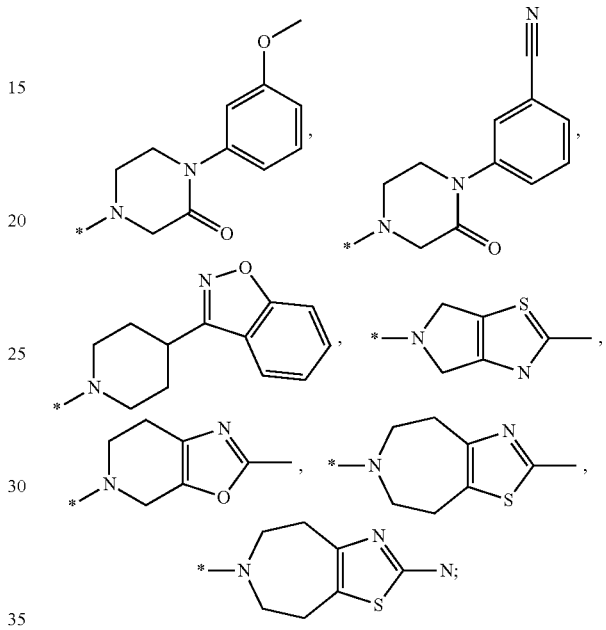

the group

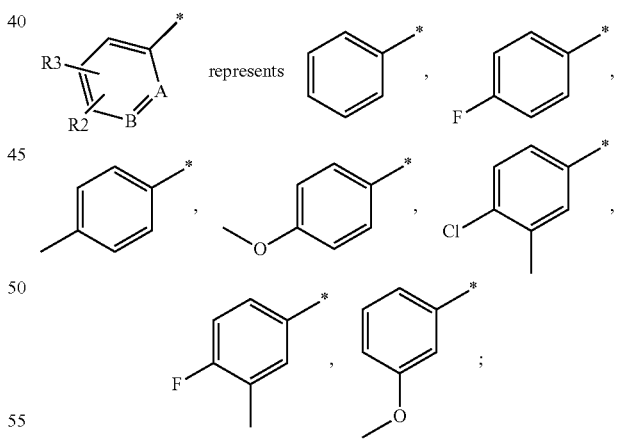

or a salt thereof, particularly a physiologically acceptable salt thereof.

TERMS AND DEFINITIONS USED

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

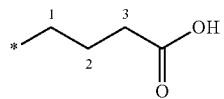

wherein the carboxy group is attached to the third carbon atom of the propyl group. The terms "1-methylpropyl-", "2,2-dimethylpropyl-" or "cyclopropylmethyl-" group represent the following groups:

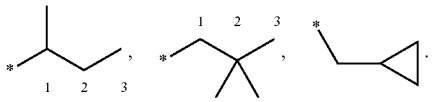

The asterisk may be used in sub-formulas to indicate the bond which is connected to the core molecule as defined.
Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.
Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2''-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.
Halogen:

The term halogen generally denotes fluorine, chlorine, bromine and iodine.
Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH (CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

Cycloalkyl:

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Aryl:

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

Heteroaryl:

The term "heteroaryl" means a mono- or polycyclic-ring systems containing one or more heteroatoms selected from N, O or S(O)ᵣ, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

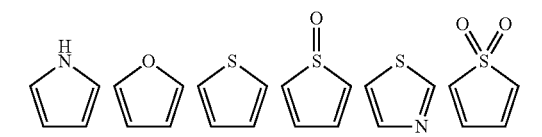

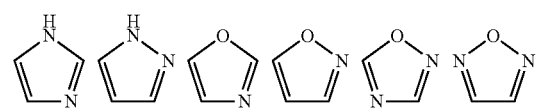

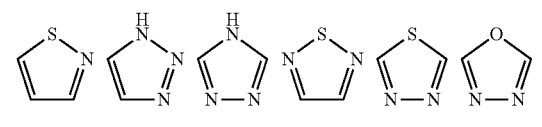

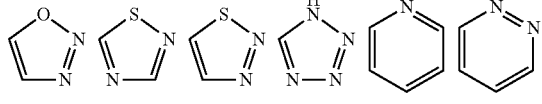

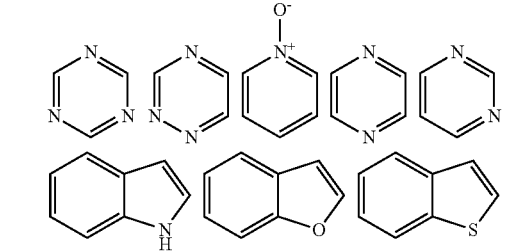

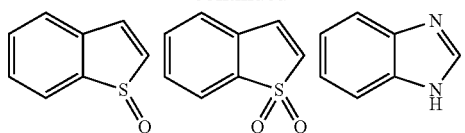

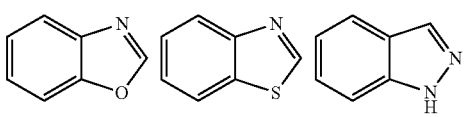

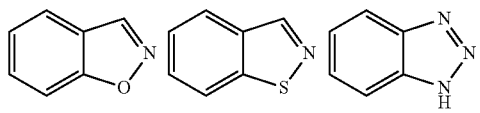

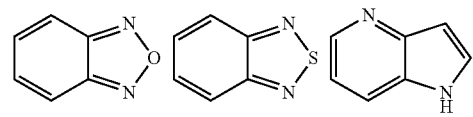

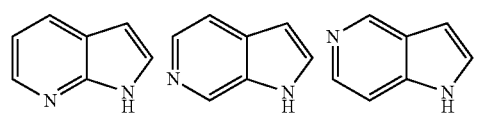

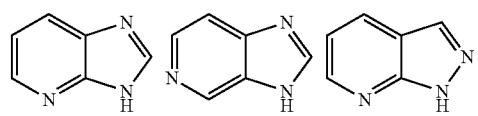

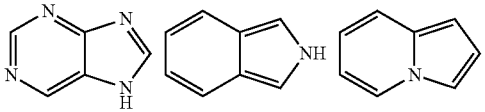

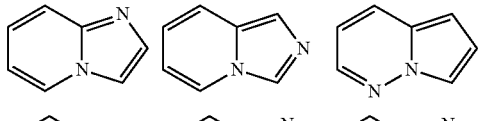

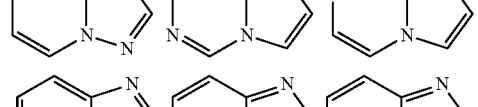

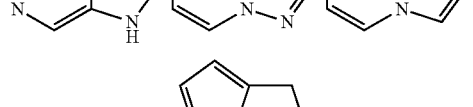

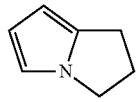

Many of the terms given above may be used repeatedly in the definition of a formula or group and in each case have one of the meanings given above, independently of one another.

General Method of Preparation

Compounds of the present invention can be prepared in accordance with techniques that are well known to those skilled in the art.

The compounds of invention can be synthesized according to the following scheme in case that R1 is an aryl or hetaryl group::

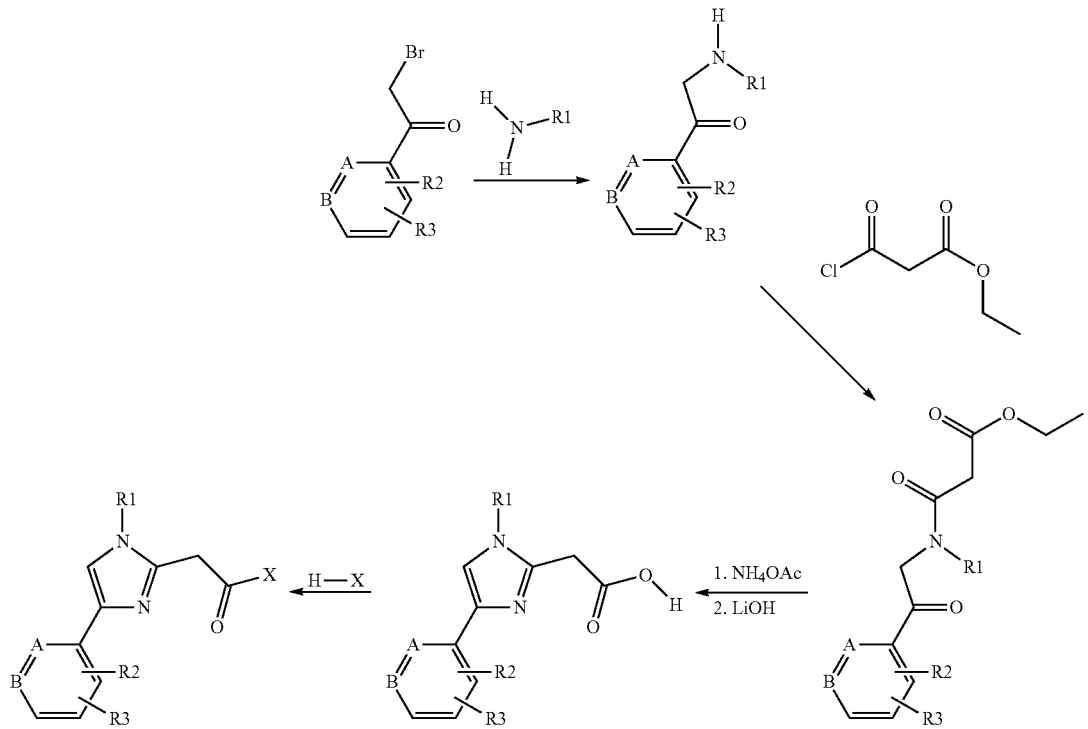

Bromacetophenone derivates were coupled with amines R1-NH2. The products, obtained were reacted with ethyl malonyl chloride to malonamic acid ethyl esters, which were cyclized to 1H-imidazoles-2yl esters using ammonium acetate. The 1H-imidazoles-2yl esters were hydrolysed with aqueous lithiumhydroxide solution. Finally, the 1H-imidazol-2-yl-acetic acid lithium salts were directly coupled with amines (HX) to provide the desired final products.

Biological Assay

The positive modulation of mGluR5 is measured in a HEK 293 cell line expressing human recombinant mGluR5 and is detected with calcium based FLIPR assay. The cells are cultured with DMEM supplemented with 10% FCS, 2 µg/mL tetracycline, 100 µg/mL hygromycin and 500 µg/mL geneticin. The cell culture media is exchanged for tetracycline-free cell culture media 3-7 days before the assay. One day before the assay the cell culture medium is exchanged to DMEM without glutamine and phenol red and supplemented with 10% FCS, 100 µg/mL hygromycin and 500 µg/mL geneticin. On the assay day, the medium of the subconfluent cultures is removed and the cells are detached by addition of 2.5 ml EDTA(0.02%) per 175 cm2 culture flask for 1 minute. The cells are resuspend in Ringer solution (140 mM NaCl, 5 mM KCl, 2.5 mM CaCl2, 1.5 mM MgCl2, 5 mM Glucose, 10 mM Hepes; adjusted to pH 7.4 with NaOH), pooled and Ringer solution added to adjust the volume to 50 mL. The cell suspension is centrifuged for 5 mM at 1500 U/min (425 g). The supernatant is removed and the cells washed a second time with 50 ml fresh Ringer solution and centrifuged again as before. The supernatant is again removed and the pellet resuspended in Ringer solution to 1,000,000 cells/ml (1×10^6 cells/mL). The cells are plated onto BD BioCoat Poly-D-Lysine 384 well plates (20,000 cells/well; 20 µl/well). The lid covered plates are then incubated until use at 37° C./10% CO2. For dye loading, 20 µl of Calcium-4 assay kit solution (prepared according to the manufacturer's description in Ringer solution) are added to the cells and the plates are incubated for 80 mM 37° C. and then 10 mM at room temperature.

Controls, Compound Dilution and Assay Execution:

Each assay plate contained wells with "high" and "low" controls:

Low controls 1% DMSO/ringer solution + basal glutamate activation (defined as 100% CTL).

High controls 10 µM CDPPB+ basal glutamate activation (defined as 200% CTL).

Test compounds are dissolved and diluted in DMSO to 100-fold the desired concentrations. In a second step, the compounds are diluted in Ringer solution such that the compounds are 4-fold more concentrated than the desired final assay concentration. The final DMSO concentration was 1%.

20 µl of each compound solution are then transferred to the assay plate and the Ca2+ kinetic is measured to determine any intrinsic compound activity. After 5 mM incubation in the FLIPR device, the second stimulation with 20 µl of glutamate in Ringer solution (glutamate concentration adjusted to approximately 5% basal stimulation of the maximal possible glutamate effect) is added and the kinetic Ca2+ response of the wells was measured for the modulation effect.

Analysis:

The peak height of the Ca release related fluorescence signal (9-66) is used for the EC50. The EC50 of the modulation is calculated over a nonlinear regression with GraphPad Prism (Table 1).

TABLE 1

| Example | EC50 [nM] |
|---|---|
| 7.01.01. | 784 |
| 7.01.02. | 109 |
| 7.02.01. | 94 |
| 7.02.02. | 114 |
| 7.02.03. | 210 |
| 7.02.04. | 375 |
| 7.02.05. | 52 |
| 7.02.06. | 93 |
| 7.02.07. | 96 |
| 7.02.08. | 32 |
| 7.02.09. | 90 |
| 7.02.10. | 328 |
| 7.02.11. | 103 |
| 7.02.12. | 39 |
| 7.02.13. | 74 |
| 7.02.14. | 87 |
| 7.02.15. | 45 |
| 7.02.16. | 70 |
| 7.02.17. | 80 |
| 7.02.18. | 67 |
| 7.02.19. | 67 |
| 7.02.20. | 70 |
| 7.02.21. | 1121 |
| 7.02.22. | 138 |
| 7.02.23. | 394 |
| 7.02.24. | 125 |
| 7.02.25. | 1443 |
| 7.02.26. | 71 |
| 7.02.27. | 94 |
| 7.02.28. | 48 |
| 7.02.29. | 33 |
| 7.02.30. | 82 |

Method of Treatment

The present invention is directed to compounds of general formula I which are useful in the treatment of a disease and/or condition wherein the activity of an mGluR5 positive modulator is of therapeutic benefit, including but not limited to the treatment of psychotic disorders, cognitive disorders and dementias.

The compounds of general formula I are useful for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia. Therefore, the present invention also relates to a compound of general formula I as a medicament.

A further aspect of the present invention relates to the use of a compound of general formula I for the treatment of a disease and/or condition wherein the activity of mGluR5 positive modulator is of therapeutic benefit.

Furthermore, the present invention relates to the use of a compound of general formula I for the treatment of psychotic disorders, cognitive disorders and dementias.

Furthermore, the present invention relates to the use of a compound of general formula I for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia.

In a further aspect of the present invention the present invention relates to methods for the treatment or prevention of above mentioned diseases and conditions, which method comprises the administration of an effective amount of a compound of general formula I to a human being.

Dosage

The dose range of the compounds of general formula I applicable per day is usually from 0.1 to 5000 mg, preferably from 0.1 to 1000 mg, more preferably from 5 to 500 mg, most preferably, 10 or 100 mg. Each dosage unit may conveniently contain from 0.1 to 500 mg, preferably 10 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole. Suitable tablets may be obtained, for example, by mixing one or more compounds according to formula I with known excipients, for example inert diluents, carriers, disintegrants, adjuvants, surfactants, binders and/or lubricants. The tablets may also consist of several layers. A further aspect of the invention is a pharmaceutical formulation including a compound of formula I in admixture with a pharmaceutically acceptable adjuvant, diluent or carrier.

Combination Therapy

In another aspect the present invention relates to a combination therapy in which an active compound according to the present invention is administered together with another active compound. Accordingly, the invention also refers to pharmaceutical formulations that provide such a combination of active ingredients, whereby one of which is an active compound of the present invention. Such combinations may be fixed dose combinations (the active ingredients that are to be combined are subject of the same pharmaceutical formulation) or free dose combinations (active ingredients are in separate pharmaceutical formulations).

Consequently, a further aspect of the present invention refers to a combination of each of the active compounds of the present invention, preferably at least one active compound according to the present invention, with another active compound for example selected from the group of antipsychotics such as haloperidol, clozapine, risperidone, quetiapine, aripripazole, and olanzapine; antidepressants such as selective serotonin re-uptake inhibitors and dual serotonin/noradrenaline re-uptake inhibitors; mood stabilizers such as lithium valproate and lamotrigine; beta-secretase inhibitors; gamma-secretase inhibitors; gamma-secretase modulators; amyloid aggregation inhibitors such as e.g. scyllo-inositol; directly or indirectly acting neuroprotective and/or disease-modifying substances; anti-oxidants, such as e.g. vitamin E, ginko biloba or ginkolide; anti-inflammatory substances, such as e.g. Cox inhibitors, NSAIDs additionally or exclusively having Aβ (Abeta) lowering properties; HMG-CoA reductase inhibitors, such as statins; acetylcholine esterase inhibitors, such as donepezil, rivastigmine, tacrine, galantamine; NMDA receptor antagonists such as e.g. memantine;

AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5, PDE9 or PDE10 inhibitors, GABAA receptor inverse agonists; GABAA alpha5 receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; muscarinic receptor M4 positive allosteric modulators; metabotropic glutamate receptor 5 positive allosteric modulators; metabotropic glutamate receptor 2 antagonists; metabotropic glutamate receptor 2/3 agonists; metabotropic glutamate receptor 2 positive allosteric modulators and other substances that modulate receptors or enzymes in a manner such that the efficacy and/or safety of the active compounds according to the invention is increased and/or unwanted side effects are reduced.

The active compounds according to the invention may also be used in combination with immunotherapies such as e.g. active immunisation with Abeta or parts thereof or passive immunisation with humanised anti-Abeta antibodies, nanobodies or antibody fragments for the treatment of the above mentioned diseases and conditions.

The active compounds according to the invention also may be combined with antipsychotics like haloperidol, flupentixol, fluspirilene, chlorprothixene, prothipendyl, levomepromazine, clozapine, olanzapine, quetiapine, risperidone, paliperidone, amisulpride, ziprasidone, aripiprazol, sulpiride, zotepine, sertindole, fluphenazine, perphenazine, perazine, promazine, chlorpromazine, levomepromazine, benperidol, bromperidol, pimozid, melperone, pipamperone, iloperidone, asenapine, perospirone, blonanserin, lurasidone.

The active compounds according to the invention also may be combined with antidepressants like amitriptyline imipramine hydrochloride, imipramine maleate, lofepramine, desipramine, doxepin, trimipramine.

Or the active compounds according to the invention also may be combined with serotonin (5-HT) reuptake inhibitors such as alaproclate, citalopram escitalopram, clomipramine, duloxetine, femoxetine, fenfluramine, norfenfluramine, fluoxetine, fluvoxamine, indalpine, milnacipran, paroxetine, sertraline, trazodone, venlafaxine, zimelidine, bicifadine, desvenlafaxine, brasofensme and tesofensine.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e. the active compounds of the present invention are provided in one dosage form and one or more of the above mentioned combination partners is provided in another dosage form. These two dosage forms may be equal dosage forms, for example a co-administration of two tablets, one containing a therapeutically effective amount of the active compound of the present invention and one containing a therapeutically effective amount of the above mentioned combination partner. It is also possible to combine different administration forms, if desired. Any type of suitable administration forms may be provided.

The active compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners may be expediently 1/5 of the normally recommended lowest dose up to 1/1 of the normally recommended dose.

The dosage forms are administered to the patient for example 1, 2, 3, or 4 times daily depending on the nature of the formulation. In case of retarding or extended release formulations or other pharmaceutical formulations, the same may be applied differently (e.g. once weekly or monthly etc.). It is preferred that the active compounds of the invention be administered either three or fewer times, more preferably once or twice daily.

Experimental Section

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

ABBREVIATIONS

RT: room temperature
THF: tetrahydrofuran
ACN: acetonitrile
MeOH: methanol
DIPEA: diisopropylamine
DEA: diethylamine
EtOAC: ethyl acetate
DMF: dimethylformamide
DCM: dichlormethane
TB TU: RBenzotriazol-1-yloxy)-dimethylamino-methylenel-dimethyl-ammonium; tetrafluoro borate
conc.: concentrated
min.: minutes DCM: dichlormethane
HCl: hydrochlorid acid
NMP: N-methyl-2-pyrrolidinone
TEA: trietylamine Analytical Methods All compounds specified in the examples below gave the correct mass spectra matching the theoretical isotope pattern. For practical reasons, only one of the major isotope peaks is given as representative data for the mass spectrum.

List of Analytical HPLC-Methods:

method A:
Agilent 1200 System
eluent:
A: water with 0.10% formicacid
B: acetonitril 0.10% formicacid
gradient:

| time in min | % A | % B | flow in ml/min |
|---|---|---|---|
| 0.00 | 95 | 5 | 1.60 |
| 0.10 | 95 | 5 | 1.60 |
| 1.75 | 5 | 95 | 1.60 |
| 1.90 | 5 | 95 | 1.60 |
| 1.95 | 95 | 5 | 1.60 |
| 2.00 | 95 | 5 | 1.60 | column: Zorbax StableBond C18, 3.0×30 mm, 1.8 μm (temperature: isocratic 20° C.).
detection: 254 nm method B:
Agilent 1200 System with diodenarraydetector and mass-detector
eluent:
A: water with 0.20% TFA
B: methanol
gradient:

| time in min | % A | % B | flow in ml/min |
|---|---|---|---|
| 0.00 | 95 | 5 | 2.20 |
| 0.05 | 95 | 5 | 2.20 |
| 1.40 | 0 | 100 | 2.20 |
| 1.80 | 0 | 100 | 2.20 | column: Sunfire C18, 3.0×30 mm, 2.5 μm (temperature: isocratic 60° C.).

method C:
Waters Alliance with DA and MS-detector
eluent:
A: water with 0.10% $NH_3$
D: methanol
gradient:

| time in min | % A | % D | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 | column: Waters XBridge C18 3.5 μm, 4.6×30 mm (temperature: isocratic 60° C.).

method D:
Agilent 1200 System with diodenarraydetector and mass-detector
eluent:
A: water with 0.20% ammonia
B: methanol
gradient:

| time in min | % A | % B | flow in ml/min |
|---|---|---|---|
| 0.00 | 95 | 5 | 2.20 |
| 0.05 | 95 | 5 | 2.20 |
| 1.40 | 0 | 100 | 2.20 |
| 1.80 | 0 | 100 | 2.20 | column: Xbridge C18, 3.0×30 mm, 2.5 μm (temperature: isocratic 60° C.).

method E:
Agilent 1200 System
eluent:
A: water with 0.10% formicacid
B: methanol 0.10% formicacid
gradient:

| time in min | % A | % B | flow in ml/min |
|---|---|---|---|
| 0.00 | 95 | 5 | 1.60 |
| 4.50 | 10 | 90 | 1.60 |
| 6.50 | 10 | 95 | 1.60 |
| 7.00 | 95 | 5 | 1.60 | column: Zorbax StableBond C18, 3.0×30 mm, 1.8 μm (temperature: isocratic 25° C.).
detection: 254 nm method F:
Agilent 1200 System with diodenarraydetector and mass-detector
eluent:
A: water with 0.20% TFA
B: methanol
gradient:

| time in min | % A | % B | flow in ml/min |
|---|---|---|---|
| 0.00 | 95 | 5 | 2.20 |
| 0.05 | 95 | 5 | 2.20 |
| 1.40 | 0 | 100 | 2.20 |
| 1.80 | 0 | 100 | 2.20 | column: Sunfire C18, 3.0×30 mm, 2.5 μm (temperature: isocratic 60° C.).

method G:
Agilent 1100 System with diodenarraydetector and mass-detector
eluent:
A: water with 0.10% TFA
B: methanol with 0.10% TFA
gradient:

| time in min | % A | % B | flow in ml/min |
|---|---|---|---|
| 0.00 | 95 | 5 | 4.00 |
| 0.15 | 95 | 5 | 4.00 |
| 1.70 | 0 | 100 | 4.00 |
| 2.25 | 0 | 100 | 4.00 | column: Sunfire C18, 4.6×30 mm, 3.5 μm (temperature: isocratic 60° C.).

Synthesis of Intermediates

6.01. Synthesis of Building Blocks

6.01.01 5,6,7,8-tetrahydro-4H-thiazolo-[4,5-d]-azepin-2-ylamine hydrobromide

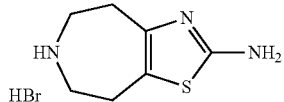 [SMILES: Br ; Nc1nc2c(s1)CCNCC2]

6.01.01.1 5-bromo-azepan-4-one hydrobromide

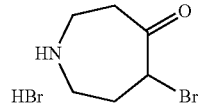

27 mL 33% HBr solution was added to 20 g hexahydro-azepin-4-one hydrochloride in 225 mL conc. acetic acid. Subsequently 6.9 mL bromine in 25 mL conc. acetic acid was added dropwise to the reaction mixture and the mixture was stirred 30 min at RT. The solvent was removed and the residue was crystallized with acetonitrile to give 27.9 g of the desired compound.
$R_t$: 0.17 min (method B), (M+H)$^+$: 192

6.01.01.2 5,6,7,8-tetrahydro-4H-thiazolo-[4,5-d]-azepin-2-ylamine hydrobromide

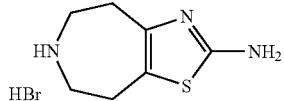 [SMILES: Br ; Nc1nc2c(s1)CCNCC2]

2.12 g thiourea was added to 8 g 5-bromo-azepan-4-one hydrobromide in 400 mL ethanol and refluxed for 5 h. The reaction was cooled down and the precipitate was filltered and dried to yield 6.95 g of the product. $R_t$: 0.61 min (method C), (M+H)$^+$: 170

By using the same synthesis strategy as for 5,6,7,8-tetrahydro-4H-thiazolo-[4,5-d]-azepin-2-ylamine hydrobromide the following compound was obtained:

| Example | Product | MS m/z [M + H]$^+$ | HPLC Method | Rt min |
|---|---|---|---|---|
| 6.01.02 | 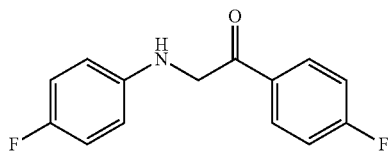 [SMILES: O=C(CNc1ccc(F)cc1)c1ccc(F)cc1] | 169 | method D | 0.61 |

6.02. Synthesis of imidazoles

6.02.01.01 1-(4-fluoro-phenyl)-2-(4-fluoro-phenylamino)-ethanone 1.3 mL 4-fluoroaniline was added to 1 g 2-bromo-4-fluoroacetophenone in 20 mL THF. The reaction was stirred 3 h at RT and 4 h at 40° C. The mixture was filtered and the filtrate diluted with ethyl acetate and extracted with water. The organic layer was dried and evaporated.

Diisopropylether was added to the residue. The precipitate was filtered and dried to yield 0.42 g desired product. $R_t$: 1.53 min (method A), (M+H)$^+$: 248

By using the same synthesis strategy as for 1-(4-fluoro-phenyl)-2-(4-fluoro-phenylamino)-ethanone the following compounds were obtained:

| Examples | Product | MS m/z [M + H]$^+$ | HPLC Method | Rt min |
|---|---|---|---|---|
| 6.02.01.02 | | 244 | method A | 1.60 |
| 6.02.01.03 | | 260 | method A | 1.52 |
| 6.02.01.04 | | 278 | method E | 5.54 |

-continued

| Examples | Product | MS m/z [M + H]⁺ | HPLC Method | Rt min |
|---|---|---|---|---|
| 6.02.01.05 | | 262 | method A | 1.63 |
| 6.02.01.06 | | 260 | method A | 1.54 |
| 6.02.01.07 | | 242 | method A | 1.50 |
| 6.02.01.07 | | 244 | method G | 1.47 |

6.02.02.01 N-(4-fluoro-phenyl)-N-(2-(4-fluoro-phenyl)-2-oxo-ethyl)-malonamic acid ethyl ester

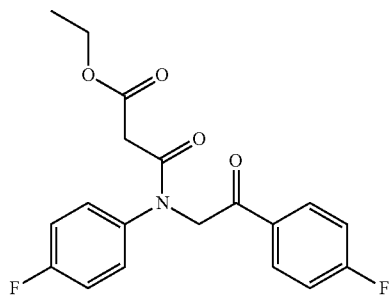 [SMILES: CCOC(=O)CC(=O)N(CC(=O)c1ccc(F)cc1)c1ccc(F)cc1]

0.23 mL ethyl malonyl chloride in 2 mL DCM was added to 420 mg 1-(4-fluoro-phenyl)-2-(4-fluoro-phenylamino)-ethanone and 0.26 mL TEA in 10 mL dichlormethane at 5° C. The reaction was stirred 2 h at RT, diluted with DCM and extracted with ethyl acetate. The organic layer was dried with magnesiumsulfate and evaporated to give 600 mg desired product.

$R_t$: 1.49 min (method A), (M+H)⁺: 362

By using the same synthesis strategy as for N-(4-fluoro-phenyl)-N-(2-(4-fluoro-phenyl)-2-oxo-ethyl)-malonamic acid ethyl ester the following compounds were obtained:

| Examples | Product | MS m/z [M + H]⁺ | HPLC Method | Rt min |
|---|---|---|---|---|
| 6.02.02.02 | | 358 | method A | 1.53 |

-continued
| Examples | Product | MS m/z [M + H]+ | HPLC Method | Rt min |
|---|---|---|---|---|
| 6.02.02.03 | 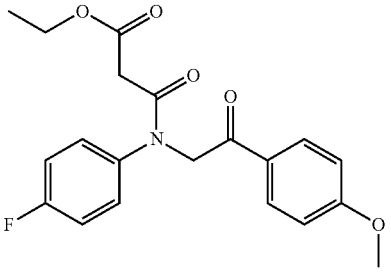 [SMILES: CCOC(=O)CC(=O)N(CC(=O)c1ccc(OC)cc1)c1ccc(F)cc1] | 374 | method A | 1.48 |
| 6.02.02.04 | 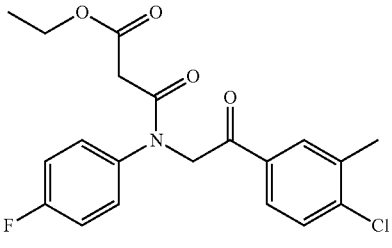 [SMILES: CCOC(=O)CC(=O)N(CC(=O)c1ccc(Cl)c(C)c1)c1ccc(F)cc1] | 392 | method A | 1.66 |
| 6.02.02.05 | 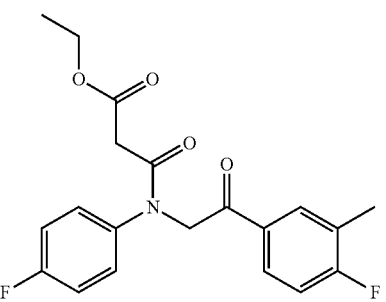 [SMILES: CCOC(=O)CC(=O)N(CC(=O)c1ccc(F)c(C)c1)c1ccc(F)cc1] | 376 | method A | 1.57 |
| 6.02.02.06 | 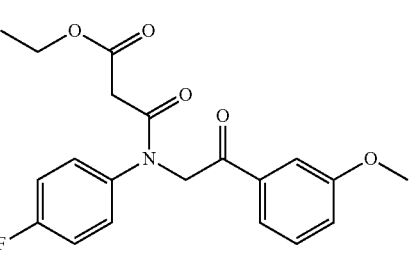 | 374 | method A | 1.50 |
| 6.02.02.07 | 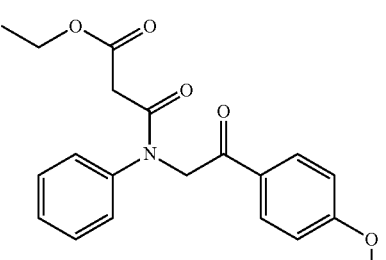 | 356 | method A | 1.44 |
| 6.02.02.08 | 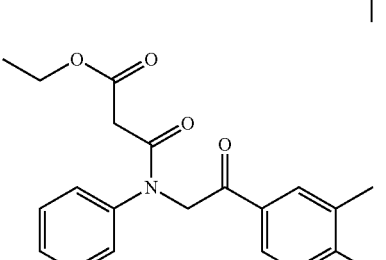 | 358 | method G | 1.45 |

6.02.03.01 (1,4-bis-(4-fluoro-phenyl)-1H-imidazol-2-yl)-acetic acid ethyl ester

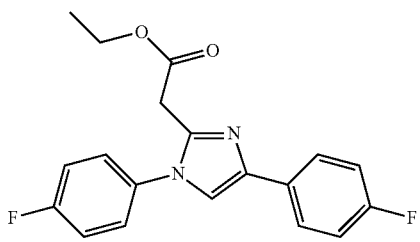 [SMILES: CCOC(=O)Cc1nc(-c2ccc(F)cc2)cn1-c1ccc(F)cc1]

1.2 g N-(4-fluoro-phenyl)-N-(2-(4-fluoro-phenyl)-2-oxo-ethyl)-malonamic acid ethyl ester and 1.8 g ammonium acetate in 20 mL concentrated acetic acid were refluxed 4 h. The reaction was evaporated. Water was added to the residue and the mixture was extracted with DCM. The organic layer was dried and evaporated. The residue was purified by chromatography on silica (100% dichlormethane) to yield 100 mg of the desired compound.

$R_t$: 1.39 min (method A), $(M+H)^+$: 343

By using the same synthesis strategy as for (1,4-bis-(4-fluoro-phenyl)-1H-imidazol-2-yl)-acetic acid ethyl ester the following compounds were obtained:

| Examples | Product | MS m/z [M + H]+ | HPLC Method | Rt min |
|---|---|---|---|---|
| 6.02.03.02 | | 339 | method A | 1.37 |
| 6.02.03.03 | | 355 | method A | 1.28 |
| 6.02.03.04 | | 373 | method A | 1.61 |
| 6.02.03.05 | | 357 | method A | 1.50 |
| 6.02.03.06 | | 355 | method A | 1.38 |

| Examples | Product | MS m/z [M + H]⁺ | HPLC Method | Rt min |
|---|---|---|---|---|
| 6.02.03.07 | | 337 | method A | 1.26 |
| 6.02.03.08 | | 339 | method G | 1.25 |

6.02.04.01 (1,4-bis-(4-fluoro-phenyl)-1H-imidazol-2-yl)-acetic acid lithium salt

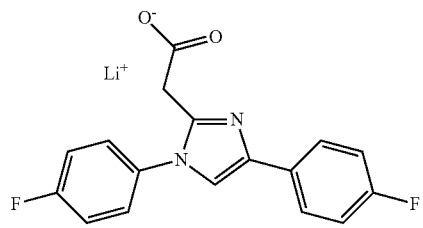 [SMILES: O=C([O-])Cc1nc(-c2ccc(F)cc2)cn1-c1ccc(F)cc1 ; [Li+]]

1.1 mL 1M aqueous lithiumhydroxide solution was added to 300 mg (1,4-bis-(4-fluoro-phenyl)-1H-imidazol-2-yl)-acetic acid ethyl ester in 10 mL dioxane. The reaction was stirred 2 h at RT and evaporated to give 270 mg desired product. $R_t$: 1.09 min (method A), (M+H)⁺: 315

By using the same synthesis strategy as for (1,4-bis-(4-fluoro-phenyl)-1H-imidazol-2-yl)-acetic acid lithium salt the following compounds were obtained:

| Examples | Product | MS m/z [M + H]⁺ | HPLC Method | Rt min |
|---|---|---|---|---|
| 6.02.04.02 | | 311 | method A | 1.08 |
| 6.02.04.03 | | 327 | method A | 1.03 |

-continued
| Examples | Product | MS m/z [M + H]+ | HPLC Method | Rt min |
|---|---|---|---|---|
| 6.02.04.04 | 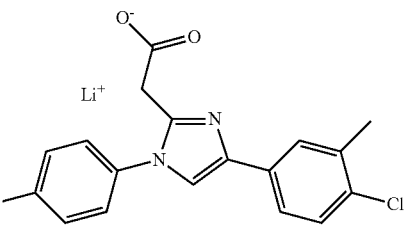 | 345 | method A | 1.28 |
| 6.02.04.05 | 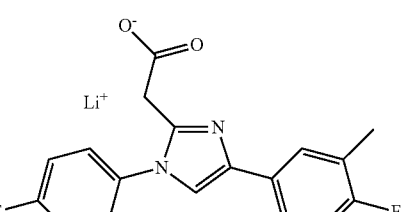 | 329 | method A | 1.17 |
| 6.02.04.06 | 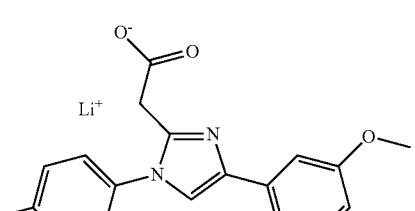 | 327 | method A | 1.03 |
| 6.02.04.07 | 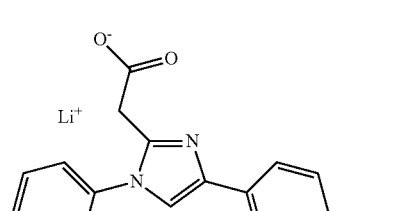 | 309 | method A | 1.03 |
| 6.02.04.08 | 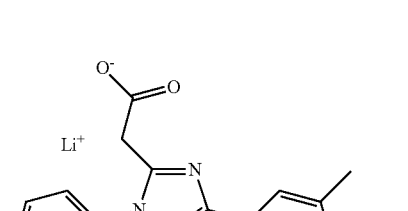 | 311 | method G | 1.08 |

7. Synthesis of target compounds

7.01.01. 2-(1,4-Bis-(4-fluoro-phenyl)-1H-imidazol-2-yl)-1-(2-methyl-6,7-dihydro-4H-oxazolo[5,4-c]pyridin-5-yl)-ethanone

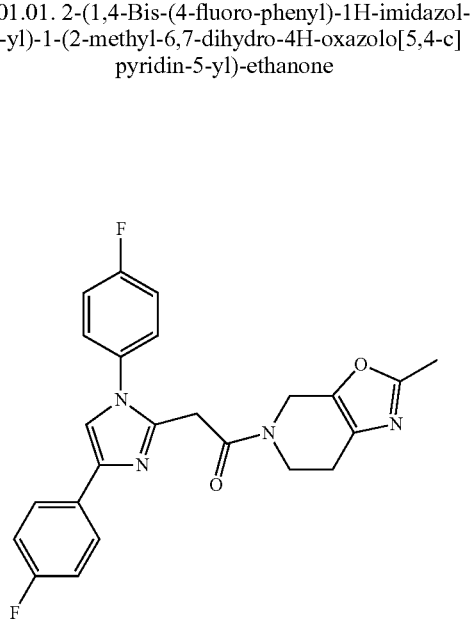

7.02.01. 2-[1,4-Bis-(4-fluoro-phenyl)-1H-imidazol-2-yl]-1-(2-methyl-4,5,7,8-tetrahydro-thiazolo[4,5-d]azepin-6-yl)-ethanone

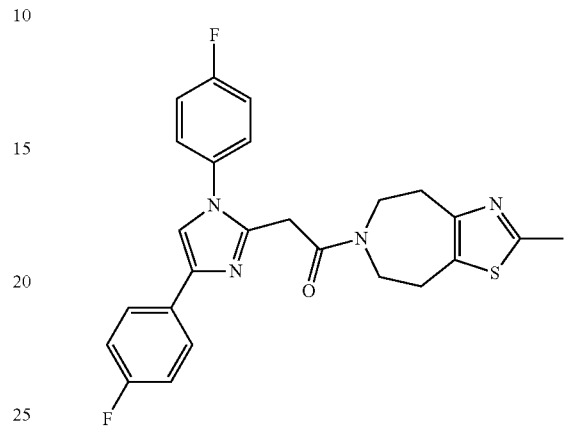

70 mg (1,4-bis-(4-fluoro-phenyl)-1H-imidazol-2-yl)-acetic acid ethyl ester, 55 mg 2-methyl-4,5,6,7-tetrahydro-oxazolo[5,4-c]pyridine hydrochloride and 0.1 mL DIPEA in 2 mL NMP was stirred 50 min at 180° C. under microwave condition. The reaction was poured into water and extracted with EtOAC. The organic layer was dried with magnesium sulfate and evaporated the residue was purified by HPLC (Waters Symmetry 50×140 mm water+0,3% HCOOH/methanoll 10% until 90% in 14 min) to yield 17 mg desired product. $R_f$: 1.10 (method A), $(M+H)^+$: 435

By using the same synthesis strategy as for 2-(1,4-Bis-(4-fluoro-phenyl)-1H-imidazol-2-yl)-1-(2-methyl-6,7-dihydro-4H-oxazolo[5,4-c]pyridin-5-yl)-ethanone the following compound was obtained:

38 mg 2-methyl-5,6,7,8-tetrahydro-4H-thiazolo[4,5-d]azepine hydrobromide was added to 40 mg (1,4-bis-(4-fluoro-phenyl)-1H-imidazol-2-yl)-acetic acid lithium salt, 45 mg TBTU, 0.06 mL DIPEA in 0.75 mL DMF. The reaction was stirred over night at RT. Water was added to the reaction and the mixture was stirred 1 h. The precipitate was filltered and dried to give 26 mg desired product. $R_f$: 4.59 (method E), $(M+H)^+$: 465

By using the same synthesis strategy as for 2-[1,4-Bis-(4-fluoro-phenyl)-1H-imidazol-2-yl]-1-(2-methyl-4,5,7,8-tetrahydro-thiazolo[4,5-d]azepin-6-yl)-ethanone the following compounds were obtained:

| Examples | Product | MS m/z $[M+H]^+$ | HPLC Method | Rt min |
|---|---|---|---|---|
| 7.01.02 | ![structure] | 466 | method A | 0.93 |

| Examples | Product | MS m/z [M + H]+ | HPLC Method | Rt min |
|---|---|---|---|---|
| 7.02.02 | | 500 | method E | 5.12 |
| 7.02.03 | | 437 | method E | 4.63 |
| 7.02.04 | | 431 | method A | 1.19 |
| 7.02.05 | | 462 | method A | 0.93 |

-continued

| Examples | Product | MS m/z [M + H]+ | HPLC Method | Rt min |
|---|---|---|---|---|
| 7.02.06 | | 461 | method A | 1.17 |
| 7.02.07 | | 499 | method F | 1.08 |
| 7.02.08 | | 494 | method F | 1.03 |
| 7.02.09 | | 433 | method F | 1.06 |

-continued

| Examples | Product | MS m/z [M + H]+ | HPLC Method | Rt min |
|---|---|---|---|---|
| 7.02.10 | | 446 | method A | 1.14 |
| 7.02.11 | | 478 | method A | 0.88 |
| 7.02.12 | | 477 | method A | 1.11 |

-continued

| Examples | Product | MS m/z [M + H]+ | HPLC Method | Rt min |
|---|---|---|---|---|
| 7.02.13 | | 515 | method F | 1.04 |
| 7.02.14 | | 449 | method F | 1.03 |
| 7.02.15 | | 496 | method A | 1.32 |
| 7.02.16 | | 497 | method A | 1.07 |

-continued

| Examples | Product | MS m/z [M + H]+ | HPLC Method | Rt min |
|---|---|---|---|---|
| 7.02.17 | | 465 | method A | 1.35 |
| 7.02.18 | | 479 | method A | 1.29 |
| 7.02.19 | | 449 | method A | 1.29 |
| 7.02.20 | | 480 | method A | 1.17 |

| Examples | Product | MS m/z [M + H]+ | HPLC Method | Rt min |
|---|---|---|---|---|
| 7.02.21 | | 447 | method A | 1.22 |
| 7.02.22 | | 477 | method A | 1.02 |
| 7.02.23 | | 460 | method A | 0.95 |
| 7.02.24 | | 459 | method A | 1.15 |

| Examples | Product | MS m/z [M + H]+ | HPLC Method | Rt min |
|---|---|---|---|---|
| 7.02.25 | | 429 | method A | 1.16 |
| 7.02.26 | | 462 | method G | 0.95 |
| 7.02.27 | | 499 | method G | 1.17 |
| 7.02.28 | | 433 | method G | 1.14 |

| Examples | Product | MS m/z [M + H]+ | HPLC Method | Rt min |
|---|---|---|---|---|
| 7.02.29 | | 461 | method G | 1.07 |
| 7.02.30 | | 510 | method F | 0.98 |
The invention claimed is:
1. A compound of formula I
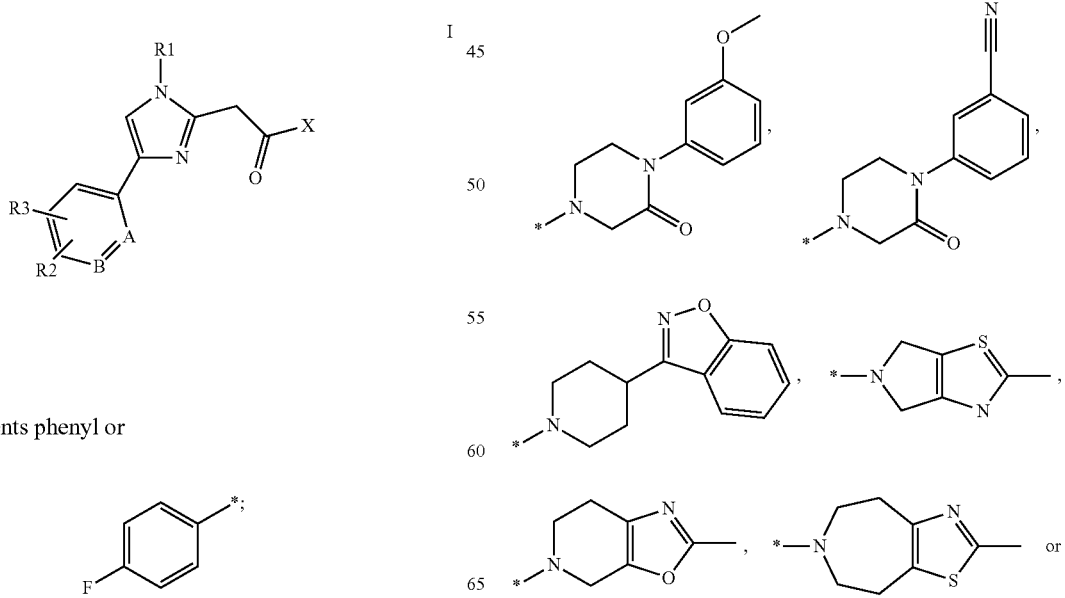
in which
R¹ represents phenyl or
X represents -continued
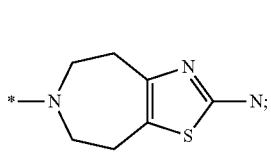
the group
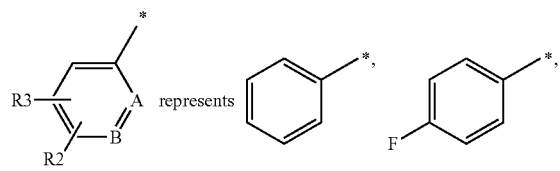
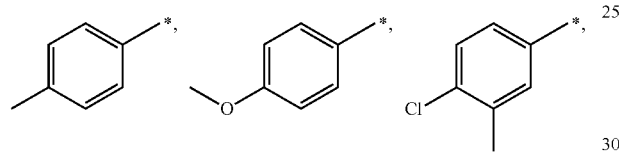
or a physiologically acceptable salt thereof.
2. A compound selected from the group consisting of
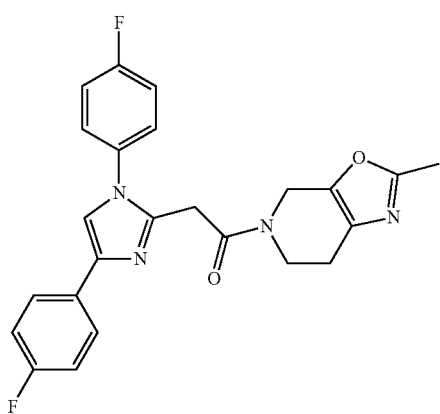 [SMILES: Cc1nc2c(o1)CN(C(=O)Cc1nc(-c3ccc(F)cc3)cn1-c1ccc(F)cc1)CC2]
-continued
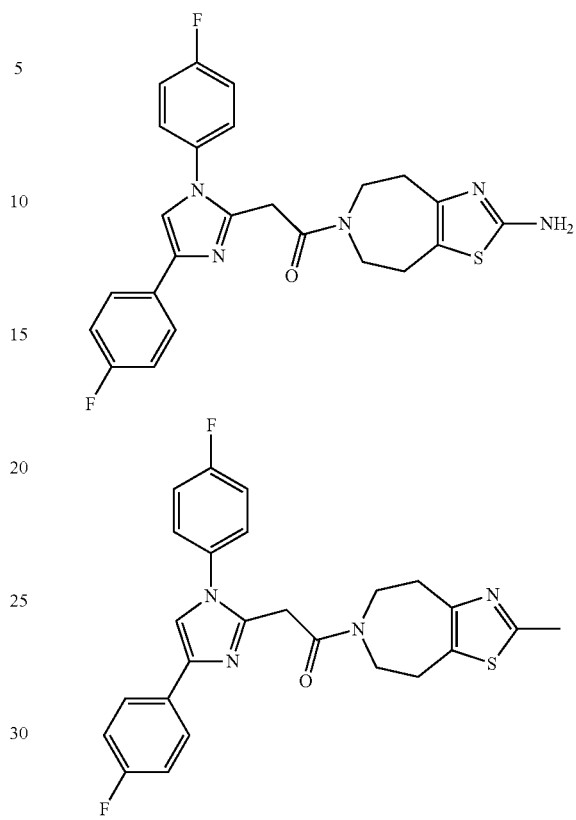
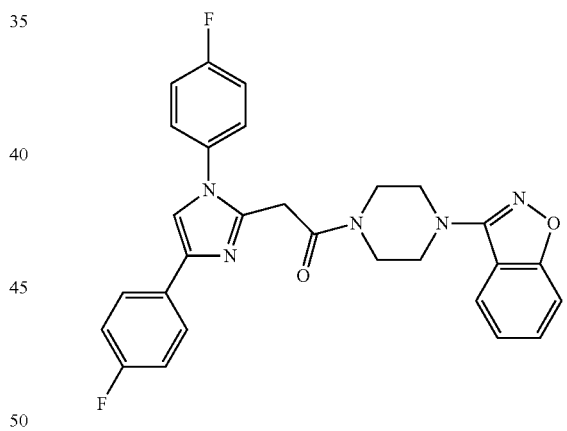
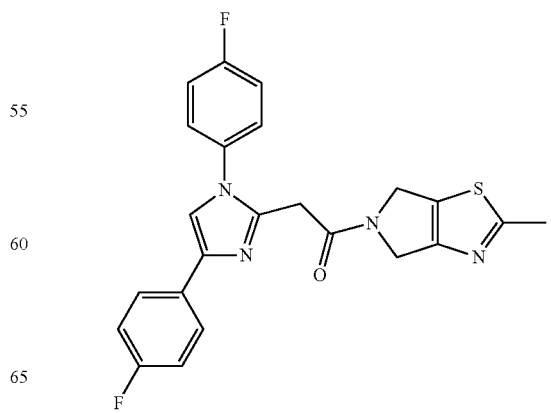

55
-continued
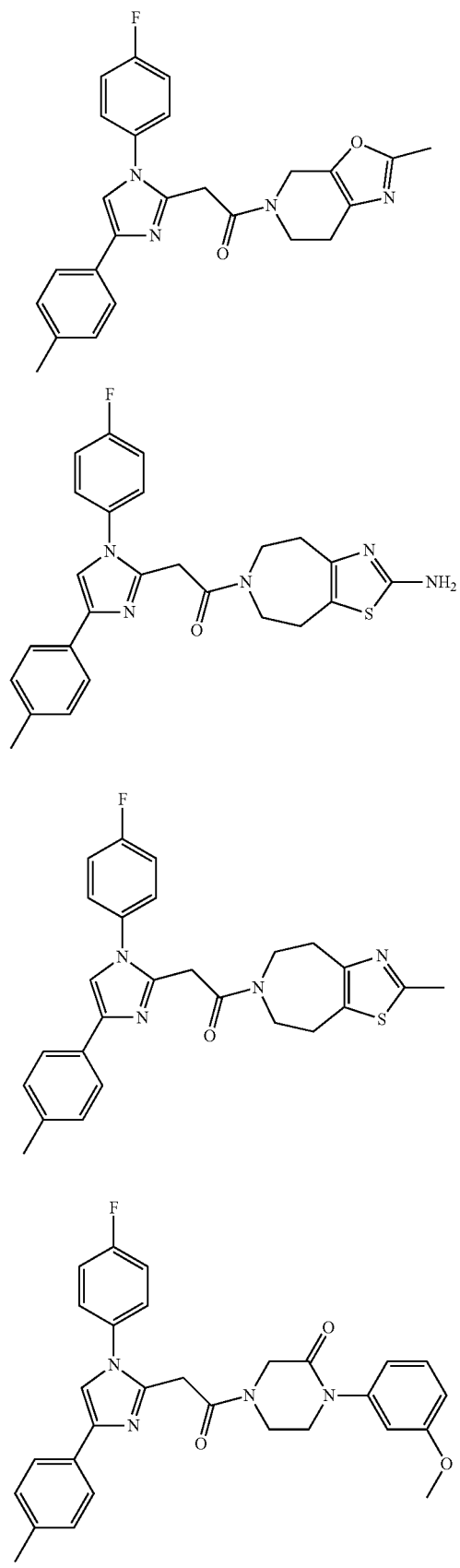
56
-continued
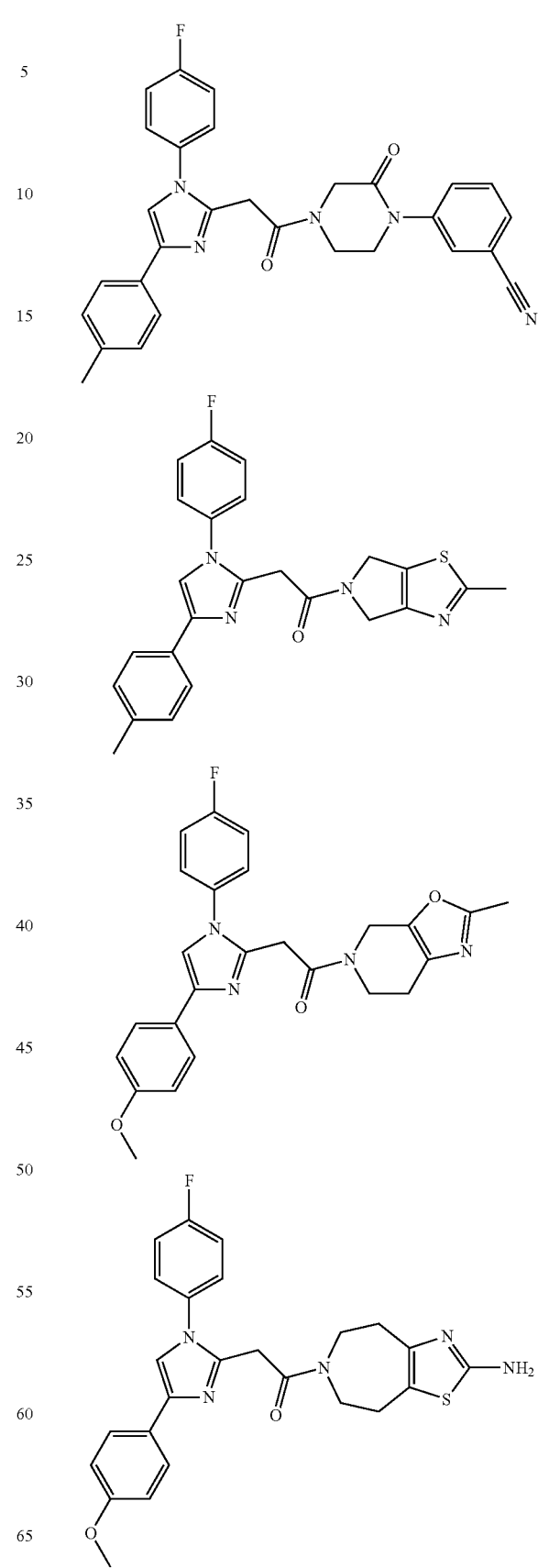

57
-continued
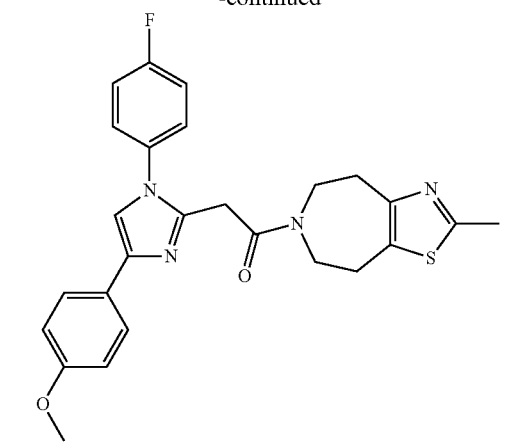
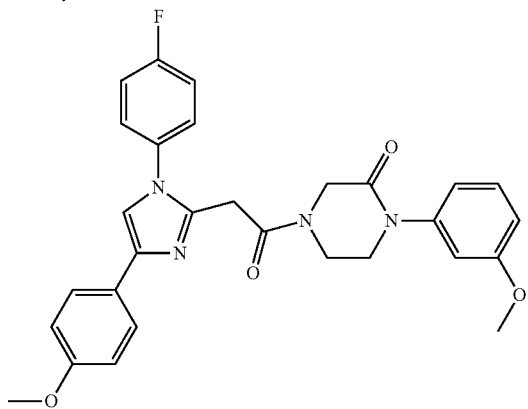
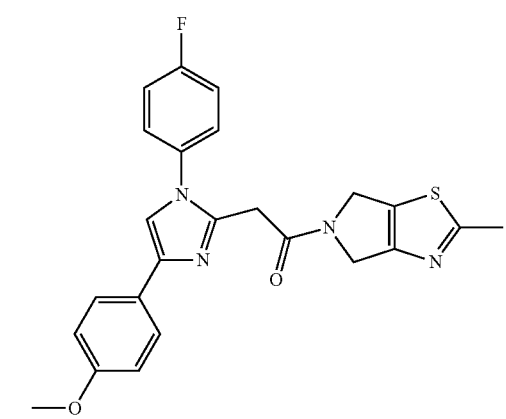
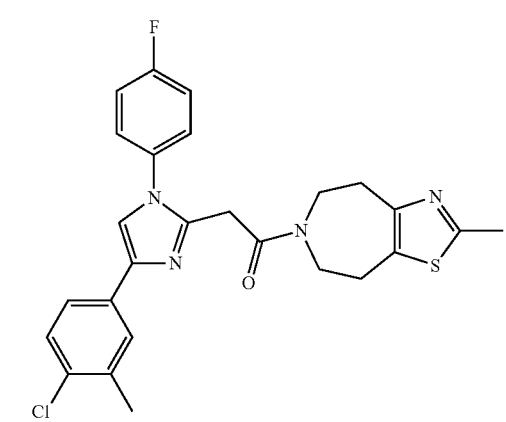
58
-continued
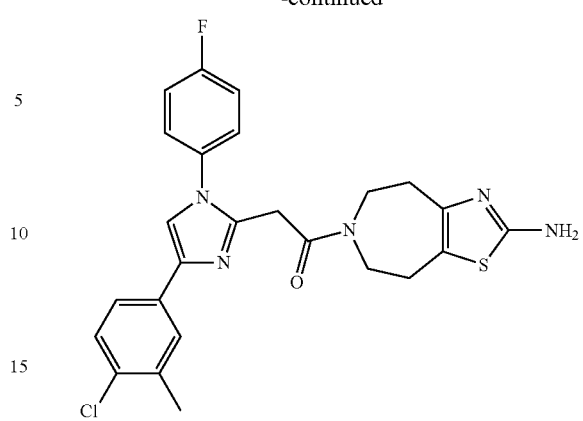
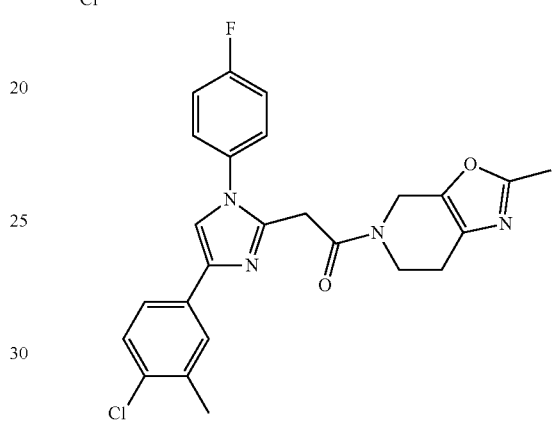
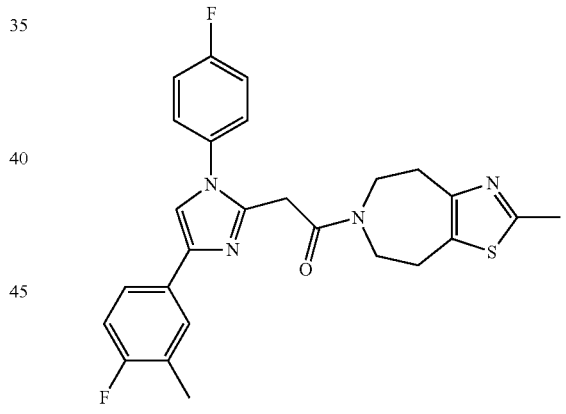
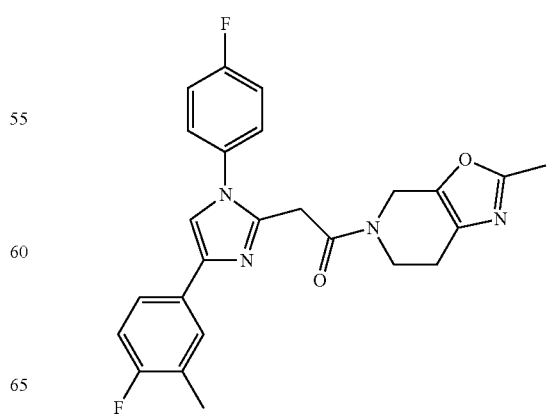

-continued
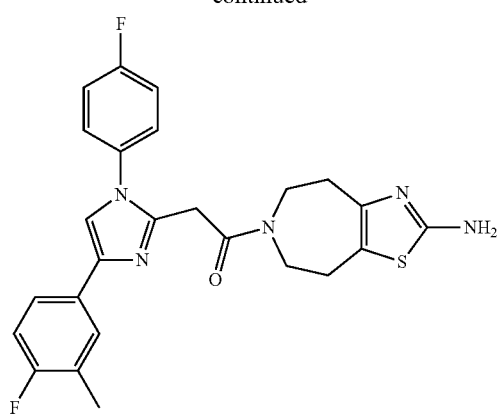
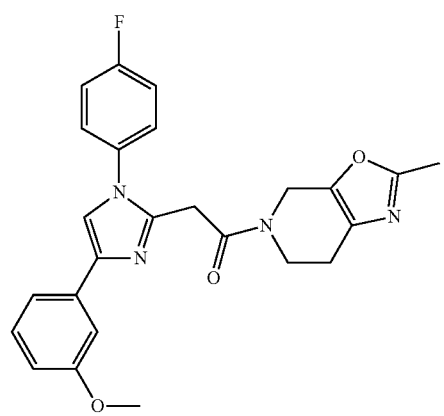
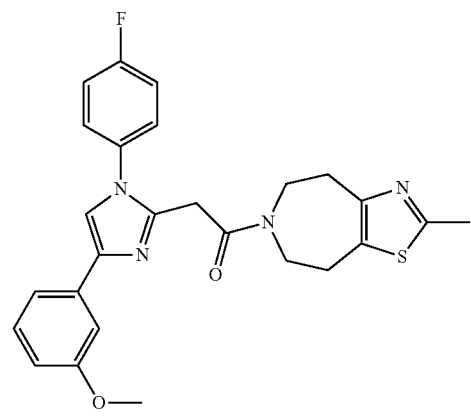
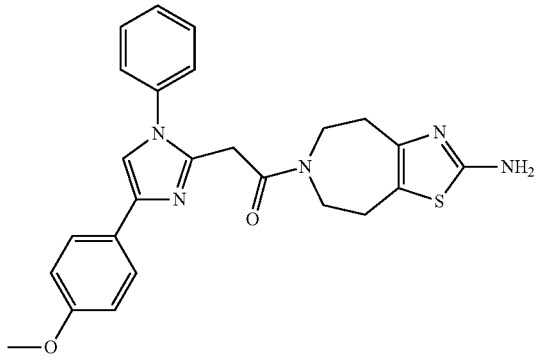
-continued
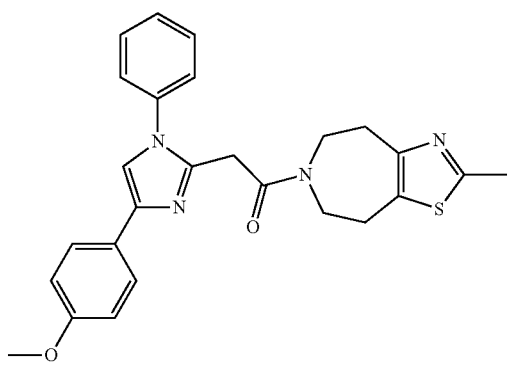
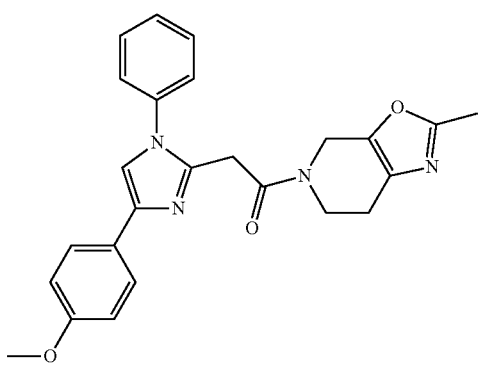
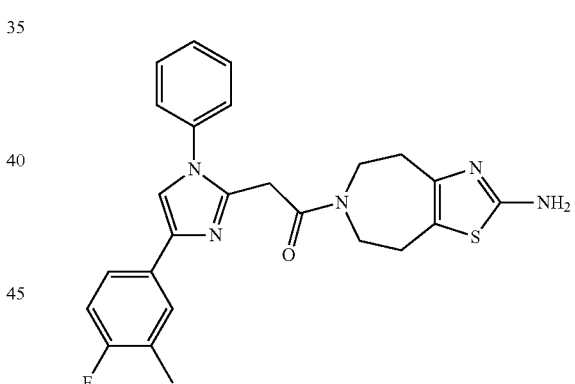
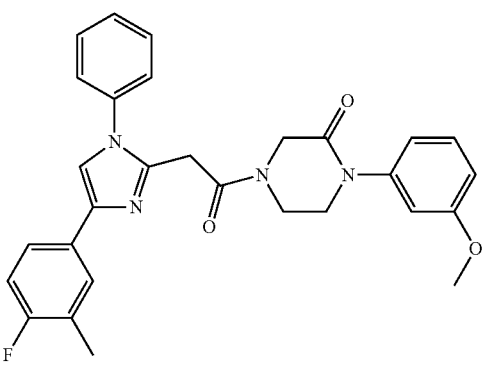

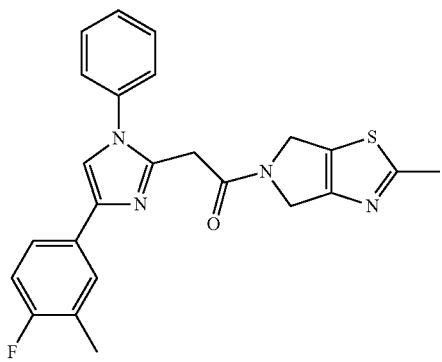

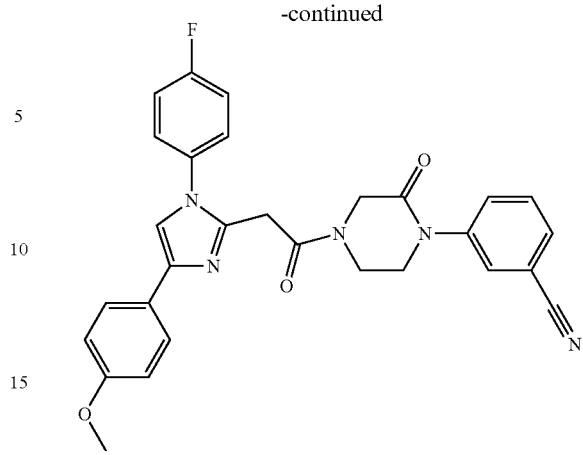

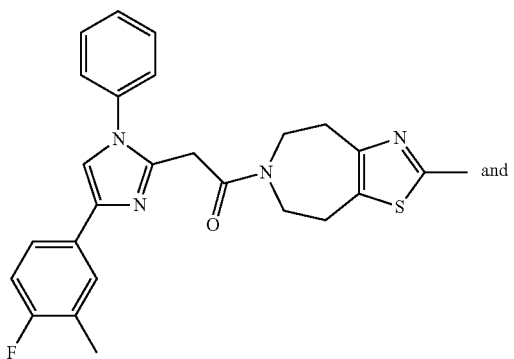 and or a physiologically acceptable salt thereof.

3. A pharmaceutical composition comprising a therapeutically effective amount of a compound according to claim 1 or a pharmaceutically acceptable salt thereof in admixture with a pharmaceutically acceptable adjuvant, diluent and/or carrier.

4. A method of treating schizophrenia, schizoaffective disorder and substance-induced psychotic disorder, age-associated learning and memory impairments or losses, post-stroke dementia, deficits in concentration, mild cognitive impairment, the cognitive dysfunction in Alzheimer's disease or the cognitive dysfunction of schizophrenia comprising administering to a patient a therapeutically effective amount of a compound according to claim 1.

\* \* \* \* \*